United States Patent [19]

Laue et al.

[11] Patent Number: 5,510,503
[45] Date of Patent: Apr. 23, 1996

[54] BISPHOSPHINES FOR ASYMMETRIC HYDROGENATION CATALYSTS

[75] Inventors: Christian Laue, Monheim; Georg Schröder, Leverkusen; Dieter Arlt, Cologne; Rolf Grosser, Leverkusen, all of Germany

[73] Assignee: Bayer Aktiengesellschaft, Leverkusen, Germany

[21] Appl. No.: 300,507

[22] Filed: Sep. 2, 1994

[30] Foreign Application Priority Data

Sep. 10, 1993 [DE] Germany ............ 43 30 730.2

[51] Int. Cl.$^6$ ............ C07F 15/00; C07F 9/02; C07C 5/02
[52] U.S. Cl. ............ 556/21; 556/136; 568/14; 568/17; 585/257; 585/277
[58] Field of Search ............ 556/21, 136; 568/14, 568/17; 585/257, 277

[56] References Cited

U.S. PATENT DOCUMENTS

| | | | |
|---|---|---|---|
| 5,187,281 | 2/1993 | Kolich et al. | 556/16 |
| 5,198,562 | 3/1993 | Noyori et al. | 556/23 |
| 5,274,167 | 12/1993 | Lange et al. | 560/40 |
| 5,286,888 | 2/1994 | Sano et al. | 556/21 |

FOREIGN PATENT DOCUMENTS

| | | |
|---|---|---|
| 104375 | 4/1984 | European Pat. Off. |
| 174057 | 3/1986 | European Pat. Off. |
| 256634 | 2/1988 | European Pat. Off. |
| 272787 | 6/1988 | European Pat. Off. |
| 366390 | 5/1990 | European Pat. Off. |
| 398132 | 11/1990 | European Pat. Off. |
| 470756 | 2/1992 | European Pat. Off. |

OTHER PUBLICATIONS

P. Stahly et al., Organomettalics, vol. 12, pp. 1467–1470 (1993).
J. Chem. Comm. 922 (1985).
R. Noyori, Modern Synthetic Methods, 115–198 (1989).

*Primary Examiner*—Porfirio Nazario-Gonzales
*Attorney, Agent, or Firm*—Sprung Horn Kramer & Woods

[57] ABSTRACT

The invention relates to novel enantiomerically pure bisphosphines of the general formula (I)

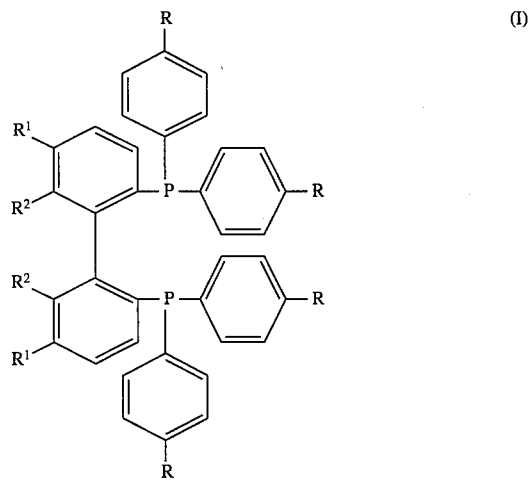

in which R, $R^1$ and $R^2$ have the meanings given in the description, a process for the preparation thereof and the use thereof in metal complexes as catalysts for asymmetric hydrogenations.

14 Claims, No Drawings

BISPHOSPHINES FOR ASYMMETRIC HYDROGENATION CATALYSTS

The invention relates to novel enantiomerically pure bisphosphines, processes for the preparation thereof and the use thereof in metal complexes as catalysts for asymmetric hydrogenations.

The use of complexes of certain bisphosphines with metals of group VIII for asymmetric hydrogenations and enantioselective hydrogen shifts is already known (cf. EP-A 398 132 and R. Noyori, Modern Synthetic Methods, 113–198 (1989)). The phosphines of the invention and the complexes prepared therefrom clearly differ in their chemical structure from the prior art compounds. It was unforeseeable that changing the substituents according to the invention would give bisphosphines and bisphosphineruthenium complexes which allow the abovementioned enantioselective reactions to be carried out with higher enantioselectivity than with the known bisphosphine complexes. EP-A 529 444 likewise describes, for example, the enantioselective hydrogenation of 2-(3-benzylphenyl)-propenoic acid to the corresponding propanoic acid with a ruthenium/bisphosphine complex (BINAP complex) with a maximum enantioselectivity of 80% e.e. The ruthenium complexes of the invention give a more significant enantioselectivity in the corresponding enantioselective hydrogenation of propenoic acid derivatives. Thus, for example, the use of the ruthenium complex with the bisphosphine furan derivative gives an enantioselectivity of about 88% e.e. The compounds of the invention of the formula (I) and the complexes formed therewith are thus particularly suitable for carrying out specific asymmetric hydrogenations in high yields and good enantioselectivity.

The invention relates to enantiomerically pure bisphosphines of the general formula (I)

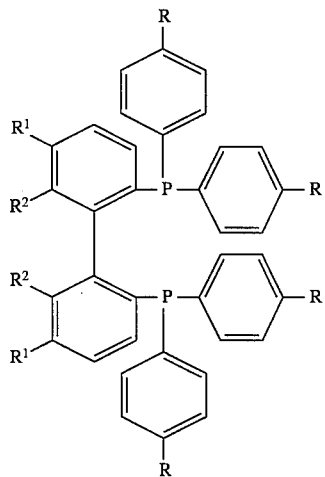

(I)

in which
represents hydrogen or alkyl having from 1 to 4 carbon atoms,
$R^1$ represents hydrogen and
$R^2$ represents chlorine or $R^1$ and $R^2$ together represent the radical of the formula

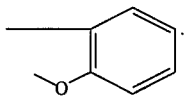

Particular preference is given to bisphosphines of the general formula (I) in which
R represents hydrogen and
$R^1$ and $R^2$ have the meanings given above.

The bisphosphines of the general formula (I) can be prepared by reacting 3-halogenophenyl compounds of the general formula (II)

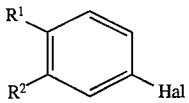

(II)

in which
$R^1$ and $R^2$ have the meanings given above and
Hal represents halogen, in particular bromine, with diphenylphosphinic chloride of the general formula (III)

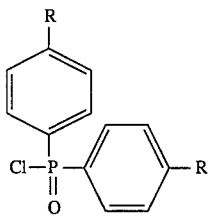

(III)

in which
R has the meaning given above, by conventional methods, for example via a Grignard reaction, to give compounds of the general formula (IV)

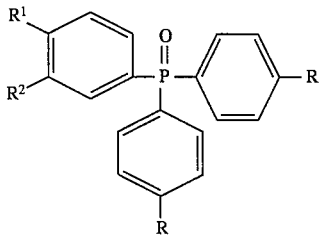

(IV)

in which
R, $R^1$ and $R^2$ have the meanings given above, and metallating these with lithium in the ortho position and subsequently reacting them with iodine to give compounds of the formula (V)

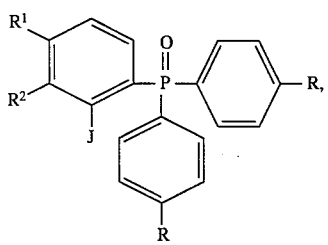

(V)

dimerizing by conventional methods (Ullmann coupling) to give racemic compounds of the general formula (VI)

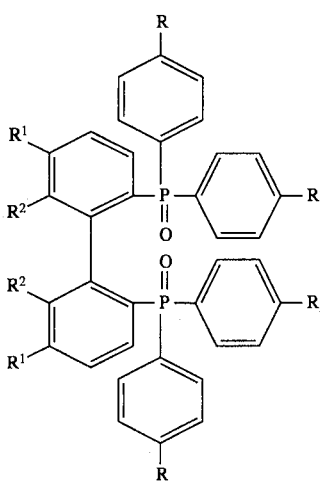

(VI)

in which

R, $R^1$ and $R^2$ have the meanings given above, and resolving these phosphine oxides into their enantiomers, for example by preparative chromatography on chiral phases or by crystallization methods using optically active acids and subsequently reducing the (S) or (R) enantiomers obtained by conventional methods to give compounds of the formula (I).

The chiral phase which is preferably used is an optically active polymer of optically active (meth)acrylic acid derivatives. Particular preference is here given to polymers of optically active N-(meth)acryloyl-amino acid derivatives, as are described in EP-379 917. Very particular preference is here given to polymers of the following optically active N-methacryloyl-amino acid amides: N-methacryloyl-L- and -D-amino acid menthylamides, with suitable amino acids being, for example, alanine, leucine, valine or other amino acids.

Eluents used for the resolution of the racemates are conventional organic solvents or solvent mixtures which swell the polymer used as adsorbent and dissolve the racemate to be resolved. Examples which may be mentioned are: hydrocarbons such as benzene, toluene or xylene, ethers such as diethyl ether, dioxane, tetrahydrofuran, halogenated hydrocarbons such as di- or trichloromethane, acetone, acetonitrile, alcohols such as ethanol or propanol or ethyl acetate or else mixtures of the stated solvents. Mixtures of toluene and tetrahydrofuran and also toluene and dioxane have proven particularly suitable.

The invention also relates to the novel intermediates of the general formula (V) and the formula (VI), where the meanings of the substituents in each case correspond to the meanings given for the formula (I), and also the process for preparing these intermediates.

The phosphorus compounds of the invention of the formula (I) form complexes with transition metals such as metals of group VIII, in particular with ruthenium, rhodium and iridium, which can be used as catalysts in asymmetric hydrogenations and also for enantioselective hydrogen shifts in prochiral allylic systems. For the hydrogenations mentioned, preference is given to ruthenium, iridium and rhodium complexes, while rhodium complexes are preferred for isomerizations. These catalysts, i.e. the complexes of a metal of group VIII and the phosphorus compounds of the formula (I), are new and likewise subjects of the present invention.

The complexes in question can be prepared in a manner known per se, for example by reacting a compound of the formula (I) in a suitable inert organic or aqueous solvent with a compound able to donate a metal of group VIII. Suitable, for example rhodium-donating, compounds which may be mentioned by way of example are organic rhodium complexes with ethylene, propylene and the like, and also with bis-olefins, for example 1,5-cyclooctadiene, 1,5-hexadiene, bicyclo[2.2.1]hepta-2,5-diene or with other dienes which form readily soluble complexes with rhodium. Preferred rhodium-donating compounds are, for example, di-chloro-bis-(1,5-cyclooctadiene)dirhodium, di-chloro-bis(-norbornadiene)dirhodium, bis-(1,5-cyclooctadiene)-rhodium tetrafluoroborate or bis(cyclooctadiene)rhodium perchlorate. An example of an iridium-donating compound which may be mentioned is di-chlorobis( 1,5-cyclooctadiene)diiridium.

Particular importance is attached to ruthenium complexes with bisphosphines of the general formula (I). Mention may be made of the ruthenium complexes of the following formulae (VII) to (XI) as typical, but not limiting, examples.

Examples of typical ruthenium complexes

| | |
|---|---|
| $Ru_2Cl_4B_2(S)$ | (VII) |
| $[Ru\ Hal\ Q\ B]^xY^e$ | (VIII) |
| $Ru\ B_n OOCR^3 OOCR^4$ | (IX) |
| $[Ru\ H_xB_n]^{me}Y_m^e$ | (X) |
| $[Ru\ Hal\ (PR^5_2R^6)B]^{(2+)Hal}{}_2^e$ | (XI) |
| $[Ru\ H\ Hal\ B_2]$ | (XII) |
| $[\ B\ Ru\ (acac)_2]$ | (XIII) | in which: acac is acetylacetonate

B represents a bisphosphine of the general formula (I)

Hal represents halogen, in particular iodine, chlorine or bromine, $R^3$ and $R^4$ are identical or different and represent alkyl having up to 9 carbon atoms, preferably up to 4 carbon atoms, which may optionally be substituted by halogen, in particular fluorine, chlorine or bromine, or represent phenyl which may optionally be substituted by alkyl having from 1 to 4 carbon atoms or represent an α-aminoalkyl acid having preferably up to 4 carbon atoms, or together form an alkylidene group having up to 4 carbon atoms, $R^5$ and $R^6$ are each identical or different and represent an optionally substituted phenyl, preferably substituted by alkyl having from 1 to 4 carbon atoms or halogen, Y represents Cl, Br, I, $ClO_4$, $BF_4$ or $PF_6$, Q is an unsubstituted or substituted benzene ring such as p-cymene, S represents a tertiary amine such as, for example, triethylamine, tri-n-butylamine or pyridine, n and m each represent 1 or 2, x represents 0 or 1, where in formula (X) n represents 1 and m represents 2 if x=0, and n represents 2 and m represents 1 if x= 1.

The complexes of the formulae (VII) to (XIII) can be prepared by methods known per se.

The complexes of the formulae (VII) and (XII) can be prepared, for example, in an analogous way by the methods described in EP-174 047 or in Chem. Comm. 922 (1985).

The complexes of the general formula (VIII) are obtained, for example, by reaction of known ruthenium complexes $[RuHal_2Q]_2$ with bisphosphines of the general formula (I) in inert organic solvents, as described, for example, in EP 366 390.

Complexes of the general formula (IX), n=1, can, for example, be obtained by methods given in EP 245 959 by reacting complexes of the general formula (VII) with corresponding carboxylic acids, preferably in alcoholic solvents.

Complexes of the formulae (IX) with n=2 and with n=1 and $R^3$, $R^4$=$CF_3$ can be prepared by the methods given in EP 272 787.

The complexes of the general formula (X) can be prepared by the method of EP-256 634.

The complexes of the general formula (XI) can be prepared by the method of EP-470 756 by reaction of the Ru precursors described therein with the bisphosphines of the invention of the general formual (I).

Complexes of the formula (XIII) can be prepared by the method given in P. Stahly et al., Organomettalics 1993, 1467 ff.

The bisphosphines of the invention in the form of their complexes with metals of group VIII and, in particular, ruthenium can be used for asymmetric hydrogenations. Suitable substrates are substituted or unsubstituted α- or β-ketoesters or α- or β-keto-amides, α- or β-amino- or α- or β-hydroxy-ketones and acetamidocinnamic acid derivatives.

Particularly suitable substrates are 2-arylpropenoic acids such as, for example, 2-(6'-methoxy-2'-naphthyl)propenoic acid, 2-(4-isobutyl)-propenoic acid and 2-(3-benzyl-phenyl)-propenoic acid and salts thereof, for example with tertiary amines.

In carrying out such hydrogenations, these complexes can be prepared first and then added to a solution of the material to be hydrogenated. However, they can alternatively also be prepared in situ, including for example in the presence of a substance to be hydrogenated.

The asymmetric hydrogenation can be carried out in a suitable organic solvent which is inert under the reaction conditions. Such solvents of which particular mention may be made are lower alcohols such as, for example, methanol or ethanol, or mixtures of such alcohols with halogenated hydrocarbons such as methylene chloride, chloroform and the like, or with cyclic ethers such as tetrahydrofuran or dioxane, and the like.

The ratio of the metals to bisphosphines of the general formula (I) advantageously lies between about 0.5 and about 2 mol, preferably at about 1 mol, of ruthenium per mole of bisphosphine ligand. The ratio of metal in the complexes to the materials to be hydrogenated advantageously lies between about 0.0005 and 1 mol %, preferably between about 0,005 and 0.6 mol %.

The asymmetric hydrogenation using the complexes of the invention is advantageously carried out at a temperature from about 0° C. to about 100° C. depending on the substrate used. This hydrogenation is also advantageously carried out under pressure, preferably at a pressure from about 5 to about 200 bar, particularly preferably from about 40 to about 140 bar.

In addition, the bisphosphine complexes of the invention can be used as catalysts for enantioselective hydrogen shifts in prochiral allylic systems. They are of particular importance, for example, in connection with the preparation of optically active compounds of the general formula (XIV)

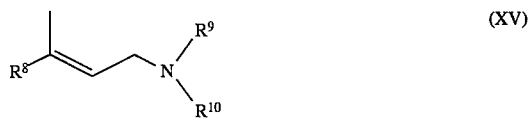

where $R^8$ represents a protected hydroxymethyl or a radical of the formula

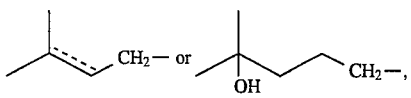

where the dotted line can represent an additional bond, and $R^9$ and $R^{10}$ are identical or different and represent a lower alkyl (1–7 carbon atoms), starting from compounds of the general formula (XV)

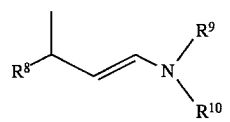

where $R^8$ $R^9$ and $R^{10}$ have the meanings given above.

The compounds (XIV) and the aldehydes obtained therefrom by hydrolysis, and also the acids and alcohols derived from these aldehydes, are, for example, of importance as intermediates in the synthesis of the side chains of vitamins E and $K_I$.

To carry out the hydrogen shifts mentioned, the phosphorus compounds of the formula (I) can be brought into contact with, for example, a rhodium- or iridium-donating compound as such in a solution of a compound to be treated. On the other hand, the phosphorus compounds of the formula (I) can first be reacted in a suitable solvent with, for example, a rhodium- or iridium-donating compound to give the corresponding catalyst complex which is then added to a solution of a compound to be treated, with the latter method being preferred.

Not only the reaction of the phosphorus compounds of the formula (I) with a, for example, rhodium- or iridium-donating compound but also the hydrogen shifts mentioned can be carried out in suitable organic solvents which are inert under the reaction conditions. Such solvents of which particular mention may be made are lower alkanols such as, for example, methanol or ethanol, aromatic hydrocarbons such as benzene or toluene, cyclic ethers such as tetrahydrofuran or dioxane, esters such as, for example, ethyl acetate, or else mixtures thereof, and the like. Furthermore, the complex formations can also be carried out in aqueous medium or in dichloromethane.

The ratio of, for example, rhodium or iridium to the ligands of the formula (I) advantageously lies between about 0.05 and about 5 mol, preferably between about 0.5 and about 2 mol, of metal per mole of ligand of the formula (I).

The amount of metal in the complexes with the ligands of the formula (I), based on the compounds to be treated for the purpose of a hydrogen shift, preferably lies between about 0,005 and about 0.5 mol %, in particular between about 0.01 and about 0.2 mol %.

The stated hydrogen shifts using metal complexes with the ligands of the formula (I) can be advantageously carried out in an inert organic solvent at a temperature from about room temperature to about 130° C. This reaction is preferably carried out at elevated temperature, i.e. depending on the solvent used either at the reflux temperature of the reaction mixture or in a closed vessel under pressure.

EXAMPLES

Abbreviations used:
cym (=cymene)=p-methyl-isopropylbenzene
THF= tetrahydrofuran DMF= dimethylformamide
all $^{31}$p spectra are {$^{1}$H} broad-band decoupled A) Preparation of the bisphosphines (I)

1) (R)-(−)- and (S)-(+)-(6,6'-Dichloro-biphenyl-2,2'-diyl)-bis-diphenylphosphine a) (3-Chloro-phenyl)-diphenylphosphine oxide (IV) A solution of 10 g of 3-bromo-chlorobenzene in 30 ml of THF is added to a boiling mixture of 1.27 g of Mg and 10 ml of THF and the mixture is boiled under reflux for a further 1 hour. Subsequently a solution of 12.4 g of diphenylphosphinic chloride in 30 ml of toluene is added dropwise at 0° C. and the mixture is stirred for a further 1 hour at room temperature. After neutralization of the reaction solution with 2N HCl, it is admixed with 150 ml of ethyl acetate and water and the organic phase is dried and concentrated. 8.82 g (54% of theoretical) of yellow crystals are obtained. m.p.: 108°–110° C.

b) (3-Chloro-2-iodo-phenyl)-diphenylphosphineoxide (V) 8.81 g of (3-chloro-phenyl)-diphenylphosphine oxide in 70 ml of THF are admixed with 14.5 ml of a 2M solution of lithium diisopropylamide in THF/n-heptane and stirred for a further 10 minutes at −76° C. A solution of 7.83 g of iodine in 30 ml of THF is added at −76° C. Subsequently the mixture is hydrolyzed with 2N HCl and extracted with ethyl acetate. The organic phase is filtered through silica gel, dried and concentrated. There remain 11.7 g (yield: 95% of theoretical) of crude product which is directly used further according to c).

c) Racemic (6,6'-dichloro-biphenyl-2,2'-diyl)-bis-diphenylphosphine oxide (VI)

A mixture of 11.4 g of (3-chloro-2-iodo-phenyl)-diphenylphosphine oxide, 5.00 g of Cu powder and 55 ml of DMF is vigorously stirred for 3 days at 140° C. with exclusion of air. The cooled reaction solution is freed of solvent and chromatographed on silica gel (eluent: ethyl acetate in cyclohexane; from 25 to 75% strength). The main fraction is precipitated by stirring in tert-butyl methyl ether. 5.42 g of crystals (67% yield) remain. $^{31}$P-NMR ([D$_6$]-DMSO): 28.0 ppm d) Resolution of the enantiomers 1 g of racemic (6,6'-dichloro-biphenyl-2,2'-diyl)-bis-diphenylphosphine oxide from Example 1c) dissolved in 100 ml of THF is introduced onto a glass column (10 cm, length 100 cm) containing swollen polymer beads of N-(methacryloyl-L-alanine-1-menthylamide) (EP-379 917) and is eluted with toluene/THF 3:1 (v/v) at a flow rate of 10 ml/min. After 15 hours the first enantiomer is eluted. The fractionated eluates are combined after analytical monitoring of enantiomeric purity. After a conventional workup, 0.4 g of the (+)-enantiomer eluted first and 0.35 g of the corresponding (−)-enantiomer are obtained.

(R)-(+)-(6,6'-Dichlorobiphenyl-2,2'-diyl)-bis-diphenylphosphine oxide (VI)

[α]$_D$=+46° (c=1, DMF)
m.p.: decomposition from 270° C.

(S)-(−)-(6,6'-Dichlorobiphenyl-2,2'-diyl)-bis-diphenylphosphine oxide (VI)

[α]$_D$=46° (c=1, DMF)
m.p.: decomposition from 270° C.

(S)-(+)-(6,6'-Dichloro-biphenyl-2,2'-diyl)-bis-diphenylphosphine (I)

A mixture of 860 mg of (S)-(−)-(6,6'-dichloro-biphenyl-2,2'-diyl)-bis-diphenylphosphine oxide, 3 ml of tributylamine, 40 ml of xylene and 0.81 ml of trichlorosilane is boiled for 16 hours under reflux. Subsequently, 13 ml of 30% strength NaOH are added at 0° C. The mixture is extracted with methylene chloride. After drying with saturated sodium chloride solution and MgSO$_4$, the solution is purified by chromatography on silica gel (from 10 to 40% strength ethyl acetate in cyclohexane). Yield: 670 mg (82% of theoretical), m.p.=230°–235° C. [α]= +51° (c=1, CHCl$_3$)

f) (R)-(−)-(6,6'-Dichloro-biphenyl-2,2'-diyl)-bis-diphenylphosphine (I)

The reaction was carried out in the same way as in e) using 916 mg of (R)-(+)-(6,6'-dichlorobiphenyl-2,2'-diyl)-bis-diphenylphosphine oxide:

Yield: 710 mg (82% of theoretical)
m.p.: 230°–235° C.
[α]$_D$= 50° (c=1, CHCl$_3$)

2) (R)- and (S)-[bis-4,4'-dibenzofuran-3,3'-diyl]'-bis (diphenylphosphine)

a) (Dibenzofuran-3-yl)-diphenylphosphine oxide (IV)

A solution of 25 g of 3-bromo-dibenzofuran in 90 ml of THF is added to a boiling mixture of 4.31 g of Mg and 10 ml of THF and the mixture is boiled under reflux for a further 1 hour. Subsequently a solution of 23.9 g of diphenylphosphinic chloride in 45 ml of THF is added dropwise at 0° C. and the mixture is stirred for a further 1 hour at room temperature.

After neutralization of the reaction solution with 1N HCl, it is admixed with 150 ml of ethyl acetate and water and the organic phase is dried with MgSO$_4$ and concentrated. The residue is stirred with tert-butyl methyl ether for 16 hours and filtered. 24.9 g of yellow crystals (65% of theoretical) remain as residue.

m.p.: 151°–155° C.

b) (4-Iodo-dibenzofuran-3-yl)-diphenylphosphineoxide (V)

9.8 g of (dibenzofuran-3-yl)-diphenyl-phosphine oxide in 100 ml of THF are admixed with 13.3 ml of a 2M solution of lithium diisopropylamide in THF/n-heptane and stirred for a further 10 minutes at −78° C. A solution of 7.9 g of iodine in 30 ml of THF is added at −76° C. Subsequently the mixture is hydrolyzed with 2N HCl, ethyl acetate is added, the solution is washed with sodium thiosulphate solution, water and saturated NaCl solution, dried with MgSO$_4$ and concentrated. 12.7 g (98% of theoretical) of crude product remain.

Purity (HPLC): 94%
m.p.: from 288 to 294° C. (purified product)

c) rac. [bis-4,4'-dibenzofuran-3,3'-diyl]-bis(diphenylphosphine oxide) (VI)

A mixture of 6.23 g of (4-iodo-dibenzofuran-3-yl)-diphenyl-phosphine oxide, 2.39 g of Cu powder and 28 ml of DMF is vigorously stirred for 16 hours at 140° C. with exclusion of air. The cooled reaction solution is filtered through Celite, freed of solvent and precipitated by stirring with tert-butyl methyl ether. 4.08 g of crystals (88% of theoretical) remain.

m.p.: 292°–300° C. (decomposition)

$^{31}$P-NMR ([D$_6$]-DMSO): 28.6 ppm (S)

d) Resolution of the enantiomers

The resolution of the enantiomers is carried out by the method described in 1d). The eluent used is a mixture of toluene/THF 2:1 (v/v). The (–)-enantiomer elutes first. (S)-(–)-(Bis-4,4'-dibenzofuran-3,3'-diyl)-bis(diphenylphosphine oxide) (VI)

m.p.: 250° C. (modification change), decomposition from 280° C.

$[\alpha]_D = -189°$ (c=1, DMF)

(R)-(+)-(Bis-4,4'-dibenzofuran-3,3'-diyl)-bis(diphenylphosphine oxide) (VI)

m.p.: 250° C. (modification change), decomposition from 280° C.

$[\alpha]_D = +196°$ (c=1, DMF)

e) (S)-(–)-(Bis-4,4'-dibenzofuran-3,3'-diyl)-bis-(diphenylphosphine) (I)

A mixture of 1.0 g (1.36 mol) of (S)-(–)-(bis-4,4'-dibenzofuran- 3,3'-diyl)-bis(diphenylphosphine oxide), 6.5 ml of tributylamine, 36 ml of xylene and 1.65 ml of trichlorosilane is boiled for 3 hours under reflux. Subsequently 10 ml of a 30% strength NaOH solution are added at 0° C. The mixture is extracted with methylene chloride.

After drying with saturated NaCl solution and MgSO$_4$, the solution is purified by chromatography on silica gel (from 10% to 30% strength ethyl acetate in cyclohexane) and precipitated by stirring in tert-butyl methyl ether.

Yield: 713 mg (75% of theoretical).

m.p.: 248°–250° C.

$[\alpha]_D = -118°$ (C=1, CHCl$_3$) $^{31}$P-NMR (CDCl$_3$): –13.4 ppm (s)

f) (R)-(+)-(Bis-4,4'-dibenzofuran-3,3'-diyl)-bis(diphenylphosphine) (I)

The reaction was carried out in the same way as in e) using 1 g of (R)-(+)-(bis-4,4'-dibenzofuran-3,3'-diyl)bis-(diphenylphosphine oxide).

Yield: 721 mg (76% of theoretical)

m.p.: 248°–250° C.

$[\alpha]_D = +119°$ (c=1, CHCl$_3$)

$^{31}$P-NMR (CDCl$_3$): –13.4 ppm (s)

B) Preparation of the catalyst complexes

1) [[(R)-(+)-4,4'-Bis-(dibenzofuran-3,3'-diyl)-bis(diphenylphosphine)]$_2$Ru$_2$Cl$_4$]·NEt$_3$ A mixture of 21.4 mg of dichloro-cycloocta-1,5-dieneruthenium(II), 59 mg of (R)-(+)-(bis-4,4'-dibenzofuran- 3,3'-diyl)-bis(diphenylphosphine), 0.17 ml of triethylamine and 1.7 ml of xylene is stirred for 4 hours at 140° C. with exclusion of air. Subsequently the solvent is removed in a high vacuum.

Yield: quantitative $^{31}$P-NMR (CDCl$_3$): 50.7 (d; J=38.4 Hz); 52.3 (d; J= 38.4 Hz)

2) [[(R)-(–)-6,6'-Dichloro-biphenyl-2,2'-diyl)-bis-diphenyl-phosphine- 1,1'-diphenyl]$_2$Ru$_2$Cl$_4$]·NEt$_3$ A mixture of 7.5 mg of dichloro-cycloocta-1,5-dieneruthenium(II), 17.4 mg of (R)-6,6'-dichlorobiphenyl-2,2'-diyl)-bis-diphenylphosphine, 0.06 ml of triethylamine and 2 ml of toluene is stirred for 4 hours at 140° C. with exclusion of air. Subsequently the solvent is removed in a high vacuum.

Yield: quantitative $^{31}$P-NMR (CDCl): 54.8 (d; J=38 Hz); 55.8 (d; J= 38 Hz)

3) Iodo-Ru-cym-[{R)-(+)-(bis-4,4'-dibenzofuran-3,3'-diyl)-bis-(diphenylphosphine)}]iodide A solution of 34 mg of (cym$_2$Ru$_2$I$_4$) in 3 ml of methanol/methylene chloride (1:1) is added to a mixture of 50 mg of (R)-(bis-4,4'-dibenzofuran-3,3'-diyl)-bis(diphenylphosphine) in 3 ml of methanol/methylene chloride (1:1), the mixture is boiled for 10 minutes under reflux with exclusion of air and is concentrated. $^{31}$P-NMR (CDCl$_3$): 41.0 (d; J=57 Hz); 23.5 (d; J=57 Hz)

4) Iodo-Ru-cym-[(R)-(–)-6,6'-dichloro-biphenyl-2,2'-diyl)-bis-diphenylphosphine] ]iodide A solution of 42 mg of (cym$_2$Ru$_2$I$_4$) in 3 ml of methanol/methylene chloride (1:1) is added to a mixture of 34 mg of (R)-6,6'-dichloro-biphenyl-2,2,-diyl)-bis-diphenylphosphine in 3 ml of methanol/methylene chloride (1:1), the mixture is boiled for 10 minutes under reflux with exclusion of air and is concentrated. $^-$P-NMR (CDCl$_3$): 43.5 (d; J=61 Hz); 26.4 (d; J=61 Hz)

5) [(–)-bis-4,4'-dibenzofuran-3,3'-diyl)-bis-(diphenylphosphine)Ru(OAc)$_2$]

211 mg of the catalyst prepared in the same manner as example B1 {[((–)-bis-4,4'-dibenzofuran- 3,3'-diyl)-bis(diphenylphosphine))$_2$Ru$_2$Cl$_4$] NEt$_3$} and 50.5 mg NaOAc was refluxed in 12 ml degassed tert.-Butanole with the exclusion of air for 12 h. The solvent was removed and the residue was extracted two times with 7 ml of degassed diethylether and filtered. The united extracts were concentrated and directly used.

$^{31}$P-NMR (CDCl$_3$): 64 ppm (s)

C) Use examples

1) Hydrogenation of 2-(3-benzyl-phenyl)-propenoic acid

A solution of 1 g 2-(3-benzyl-phenyl)-propenoic acid and 460 mg of triethylamine in 15 ml of degassed methanol is prepared with the exclusion of air and is admixed with 21 mg of the catalyst prepared in Example B1. The mixture is subsequently hydrogenated for 48 hours at 100 atm at room temperature.

Yield: quantitative Enantiomeric excess: 89% e.e. ((–)-form) (The determination of the enantiomeric excess is carried out after oxidation to 2-(3-benzoyl-phenyl)-propionic acid by HPLC on a chiral phase as described in EP-A-529 444).

2) Hydrogenation of 2-(3-benzyl-phenyl)-propenoic acid
A solution of 1 g of 2-(3-benzyl-phenyl)-propenoic acid in 460 mg of triethylamine in 15 ml of degassed methanol is admixed, with exclusion of air, with half of the catalyst prepared in Example B2. The mixture is subsequently hydrogenated for 48 hours at 90 atm at room temperature.

Conversion and yield: quantitative
Enantiomeric excess: 84.2% e.e. ((−)-form)
(The determination of the enantiomeric excess is carried out by HPLC as described in Use Example 1).

3) Hydrogenation of methyl acetoacetate 1.0 g of methyl acetoacetate is dissolved in 15 ml of oxygen-free MeOH/ $CH_2Cl_2$ (1:1). Subsequently half of the catalyst prepared in Example B3 is added and the solution is transferred into an autoclave flushed with argon. The mixture is subsequently hydrogenated for 2 days at room temperature and a hydrogen pressure of 90 atm. For the workup, the solvent is removed.

Conversion ($^1$H-NMR): 100%
Determination of the enantiomeric excess:
A mixture of 20 mg of the product from Example C3, 1 ml of $CH_2Cl_2$ abs., 50 mg of (+)-α-methoxy-α-(trifluoromethyl)phenylacetyl chloride and 0.26 ml of pyridine is stirred overnight at room temperature and analyzed by gas chromatography:
Enantiomeric excess: 98.3% e.e. ((−)-form).

4) Hydrogen of 2-(3-benzyl-phenyl)-propenoic acid A solution of 1 g of 2-(3-benzyl-phenyl)-propenoic acid in 15 ml of degassed methanol is prepared with exclusion of air and is admixed with half the product from Example B4. The mixture is subsequently hydrogenated for 48 hours at 100 atm at room temperature. Yield and conversion: quantitative Enantiomeric excess: 83% e.e. ((−)-form) (The determination of the enantiomeric excess is carried out as described in Example C1)

5) Hydrogenation of 2-(3-benzyl-phenyl)-propenoic acid A solution of 1 g of 2-(3-benzyl-phenyl)-propenoic acid and 460 mg of triethylamine in 15 ml of degassed methanol is admixed, with exclusion of air, with one third of the catalyst prepared in Example B3. The mixture is subsequently hydrogenated for 48 hours at 90 atm at room temperature. Conversion and yield: quantitative Enantiomeric excess: 87% e.e. ((−)-form)

6) Hydrogenation of 2-(3-benzyl-phenyl)-propenoic acid A solution of 1 g of 2-(3-benzyl-phenyl)-propenoic acid and 460 mg of triethylamine in 15 ml of degassed Methanol is admixed, with the exclusion of air, with 30 mg of the catalyst prepared in Example B5. The mixture is subsequently hydrogenated for 60 h at 90 atm at room temperature. Conversion and yield: quantitative Enantiomeric excess: 87.6 % e.e. (+)-form 7) Hydrogenation of 2-(3-benzyl-phenyl)-propenoic acid by in situ build [Ru ((−)-bis-4,4'-dibenzofuran-3,3'-diyl)-bis-(diphenyl-phosphine)) (acac)$_2$] A solution of 22 mg Ru(acac)3, 43 mg (−)-bis-4,4'-dibenzofuran- 3,3'-diyl)-bis-(diphenyl-phosphine), 2 g 2-(3-benzyl-phenyl)-propenoic acid and 0.92 g of triethylamine in 30 ml of degassed Methanol is hydrogenated at room temperature for 48 h at 90 atm. Conversion and yield: quantitative Enantiomeric excess: 83.0 e.e. (+)-form

We claim:
1. An enantiomerically pure bisphosphine of the formula

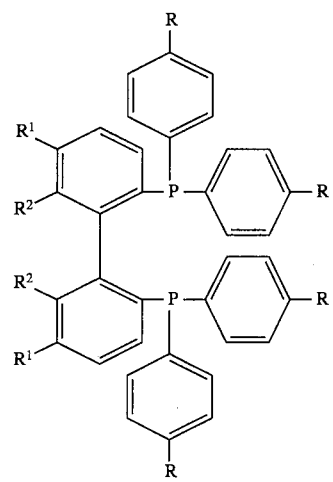

in which

R is hydrogen or alkyl having from 1 to 4 carbon atoms, $R^1$ is hydrogen and $R^2$ is chlorine, or $R^1$ and $R^2$ together form the radical of the formula

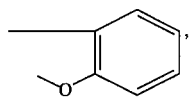

in their (R)- or (S)-form.

2. A bisphosphine according to claim 1, in which R and $R^1$ are hydrogen and $R^2$ is chlorine, or $R^1$ and $R^2$ together form the radical of the formula

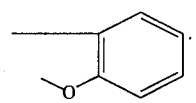

3. A process for preparing a bisphosphine according to claim 1, which comprises reacting a halogenophenyl compound of the formula

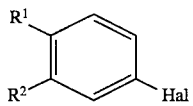

in which

Hal is halogen, with a diphenylphosphinic chloride of the formula

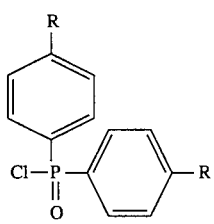

to produce a compound of the formula

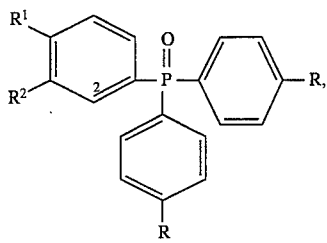

(IV)

with lithium metallating the compound of the formula (IV) in the 2-position, subsequently reacting with iodine to form a compound of the formula

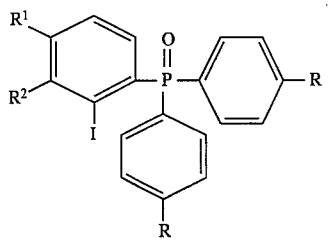

(V)

dimerizing the compound (V) to produce a racemic mixture of a phosphine oxide of the formula

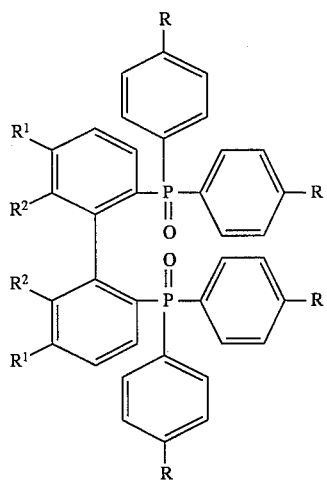

(VI)

resolving the phospine oxide of the formula (VI) into its (S) or (R) enantiomer and reducing the enantiomer to produce a compound of the formula (I).

4. A compound of the formula

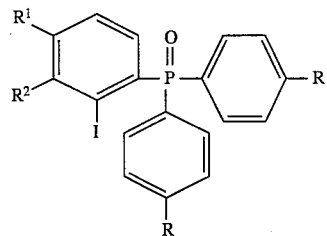

(V)

in which

R is hydrogen or alkyl having from 1 to 4 carbon atoms, $R^1$ is hydrogen and $R^2$ is chlorine, or $R^1$ and $R^2$ together form the radical of the formula

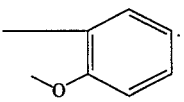

5. A compound of the formula

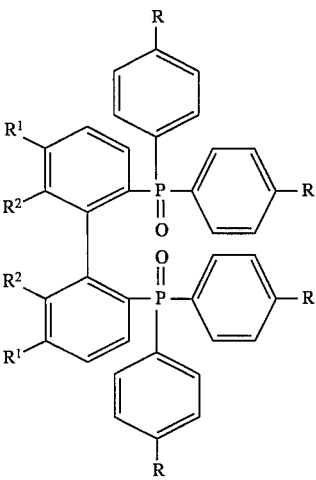

in which

R is hydrogen or alkyl having from 1 to 4 carbon atoms, $R^1$ is hydrogen and $R^2$ is chlorine, or $R^1$ and $R^2$ together form the radical of the formula

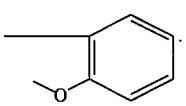

6. A complex of a bisphosphine according to claim 1 and a metal of group (VIII).

7. A complex of a bisphosphine according to claim 1 and Ru, Rh or Ir.

8. A complex of a bisphosphine according to claim 1 and Ru.

9. In effecting an asymmetric hydrogenation or an enantioselective H shift in a prochiral system employing a complex of a bisphosphine oxide, the improvement wherein said complex is a complex according to claim 6.

10. A method comprising hydrogenating a 2-aryl-propenoic acid or salt thereof in the presence of a complex according to claim 8.

11. A method comprising hydrogenating a compound selected from the group consisting of
   a) a keto group-containing compound selected from the group consisting of
      a1) an α- or β-ketoester or ketoamide, and
      a2) an α- or β-aminoketone or -hydroxy-ketone, thereby to form the corresponding alcohol, and
   b) the C-C double bond of an allylamine, allyl alcohol or acetamidocinnamic acid derivative,
in the presence of a complex according to claim 8.

12. In effecting an asymmetric hydrogenation in the presence of hydrogen or an enantioselective H shift in a prochiral system employing a complex of a bisphosphine, the improvement wherein said complex is a complex according to claim 6.

13. A method of hydrogenating a 2-aryl-propenoic acid or a salt thereof which comprises hydrogenating said compound in the presence of a complex according to claim 8 and hydrogen.

14. A method of hydrogenating a compound selected from the group consisting of
- a) a keto group-containing compound selected from the group consisting of
   - a1) an α- or β-ketoester or ketoamide, and
   - a2) an α- or β-aminoketone or -hydroxy-ketone, thereby to form the corresponding alcohol, and
- b) the C-C double bond of an allylamine, allyl alcohol or acetamidocinnamic acid derivative, which comprises by hydrogenating said compound in the presence of a complex according to claim 8 and hydrogen.

* * * * *